United States Patent [19]

Fischer et al.

[11] Patent Number: 5,304,470
[45] Date of Patent: Apr. 19, 1994

[54] PROCESS FOR THE ENZYMATIC PREPARATION OF PROTECTED AND UNPROTECTED DI- AND OLIGOPEPTIDES IN AQUEOUS SOLUTIONS

[75] Inventors: Andreas Fischer, Bonn, Fed. Rep. of Germany; Alexander Schwarz, Rehovot, Israel; Christian Wandrey, Juelich, Fed. Rep. of Germany; Guenter Knaup, Bruchkoebel, Fed. Rep. of Germany; Andreas Bommarius, Frankfurt, Fed. Rep. of Germany; Karl-Heinz Drauz, Freigericht, Fed. Rep. of Germany

[73] Assignees: Forschungszentrum Juelich GmbH, Juelich; Degussa AG, Frankfurt am Main, both of Fed. Rep. of Germany

[21] Appl. No.: 823,956

[22] Filed: Jan. 23, 1992

[30] Foreign Application Priority Data

Jan. 23, 1991 [DE] Fed. Rep. of Germany ....... 4101895

[51] Int. Cl.$^5$ ............ C12P 21/00; C07K 01/14; C07K 01/06
[52] U.S. Cl. .................. 435/68.1; 530/335; 530/338
[58] Field of Search ............... 435/68.1; 530/335, 338

[56] References Cited

U.S. PATENT DOCUMENTS 5,057,415 10/1991 Schuetz et al. ............... 435/68.1

FOREIGN PATENT DOCUMENTS 618842 8/1980 Switzerland .

OTHER PUBLICATIONS

Schellenberger et al., (1988) 2884–2889, "Specific Water-Soluble Substrates for Chymotrypsin: Attempts for Compensating Diminished $P_1$-$S_1$ Interactions".
Atassi et al., 546–553, "Reaction of Proteins with Citraconic Anhydride".
Chemical Abstracts, vol. 103, Oct., 1985: Jakubke et al., "Peptides", p. 587, Abst. #121,717.
Chemical Abstracts, vol. 114, Feb., 1991: Gololobov et al., "Increased Nucleophile Reactivity of Amino Acid Beta-Naphthylamides in Alpha-Chymotrypsin-Catalyzed Peptide Synthesis", p. 336, Abst. #58,418.
Hughes et al, "Identification of Two Related Pentapeptides From the Brain With Potent Opiate Agonist Activity", *Nature*, 258:577, (1975).
Kuhl et al, (1984) *Pharmazie*, 39,H.4, 280.
Könnecke et al, (1985) *Monat. Chem.*, 116, 111–117.
Schellenberger et al. (1986) *Biochim Biophys Acta*, 869, 54–60.
Gololobov et al, (1990) *Biochem. B Cophys Acta.*, 1041, 71–78.
Fruton (1982) *Adv. Enzymol. Retato Areas Mol. Biol.*, 53, 239–306.
Morihara (1987) *TIBTECH.*, 5, 164–170.
Jakubke et al, (1985) *Angew. Chem. Int Ed. Eng.*, 24(2), 85–93.
Kasche (1989) in "Proteolytic Enzymes", Begnon, Ed., IRL Press, NY, 125–143.

*Primary Examiner*—Douglas W. Robinson
*Assistant Examiner*—Jon P. Weber
*Attorney, Agent, or Firm*—Foley & Lardner

[57] ABSTRACT

Protected and unprotected di- or oligopeptides are synthesized by reacting an N-terminally protected α-amino acid alkyl ester or peptide alkyl ester of the formula X—E—R$^1$ with an amino acid or a di- or oligopeptide or a derivative thereof of the formula H$_2$N—Q—R$^2$ in aqueous solution in the presence of a hydrolase, and, removing protective groups from the reaction product separated from the reaction mixture, where E is the residue of an α-amino acid or of a di- or oligopeptide, R$^1$ is lower alkyl and X is a group which carries a charge or is polar at the pH values used for the reaction and which increases the solubility by a factor >5 compared with compounds wherein X=H, Q is the residue of an amino acid or of a di- or oligopeptide, and R$^2$ is an optionally esterified or amidated acid group. In a preferred embodiment, the peptide or (α-)amino acid ester concentration is greater than 50 mM, wherein in a particularly preferred embodiment, the concentration ranges from 100 to 1000 mM with approximately comparable nucleophile and electrophile concentrations. The preferred substrate/enzyme ratios are >10$^5$ M/M or >10$^3$ M/M when papain is employed. Phthalyl, maleyl or citraconyl radicals and their derivatives or N-betainyl compounds are envisaged for use radicals (X) in the electrophilic component.

20 Claims, 1 Drawing Sheet

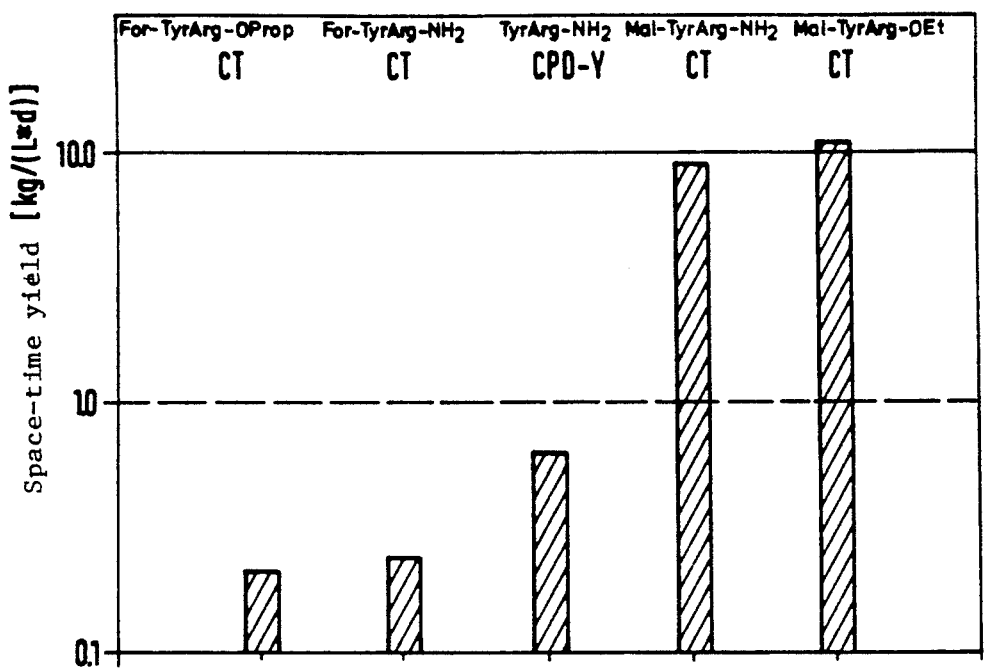
FIG. 1
Space-time yield achieved with different protective groups and enzymes (with residence time of 15 min and appropriate enzyme concentration)
FIG. 2
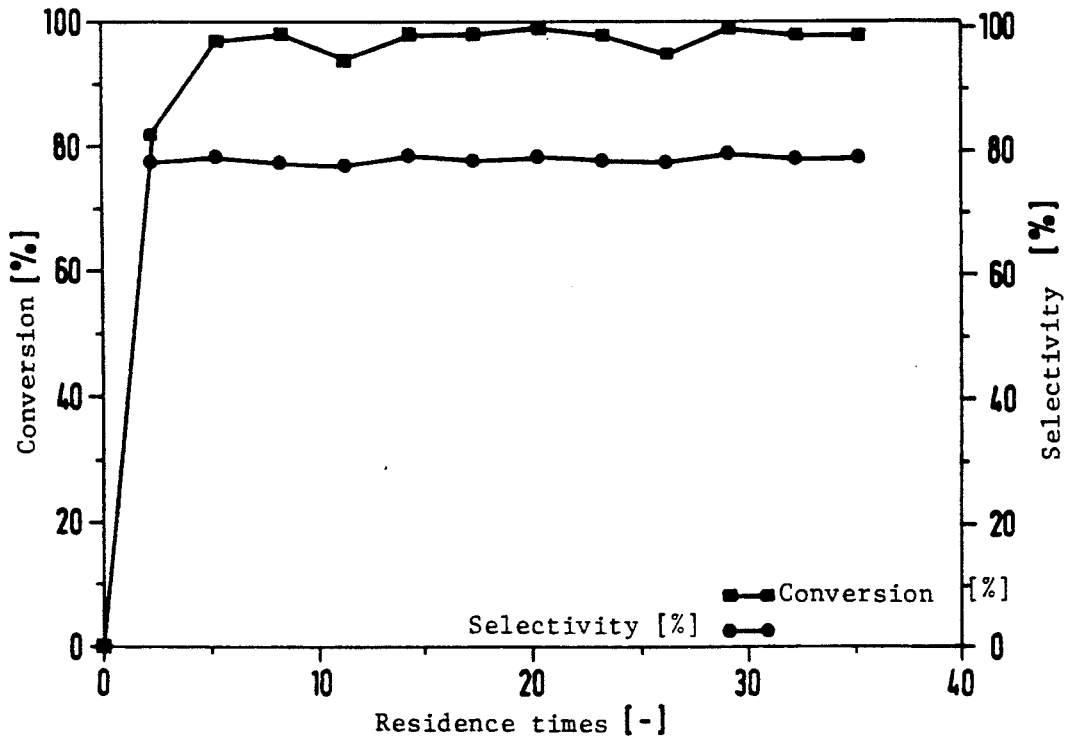

PROCESS FOR THE ENZYMATIC PREPARATION OF PROTECTED AND UNPROTECTED DI- AND OLIGOPEPTIDES IN AQUEOUS SOLUTIONS

BACKGROUND OF THE INVENTION

The present invention relates to a process for the enzymatic preparation of protected di- or oligopeptides in highly concentrated, aqueous solutions.

Synthetic short-chain peptides are increasingly being used in pharmacology and parenteral nutrition. Exemplary of such pharmacologically active dipeptides is kyotorphin (L-Tyr-L-Arg) which promotes the release of enkephalins. Enkephalins are endogenous substances which exhibit an analgesic and sedative effect in the brain (Hughes, 1975).

The chemical and optical purity of peptides intended for such a use are very critical. Accordingly, it is increasingly common to employ regio- and stereospecific enzymatic peptide syntheses to produce such peptides. Such syntheses usually entail reacting, under kinetic control, N-protected amino acid alkyl esters in the presence of a hydrolase with an amino acid derivative or a di- or oligopeptide derivative with a free amino group. When such reactions are carried out in the presence of water, the alkyl esters will also undergo hydrolysis as this reaction is thermodynamically favored.

A disadvantage associated with this process is that the enzymes employed in these syntheses are only active and stable in the presence of water, while the substrates are generally only slightly soluble in water. Adding organic solvents in order to increase the solubility of the substrates usually at least partially inactivates an enzyme and causes a decrease in its stability. As a result, prior to the instant invention, the maximum substrate concentration employed has usually been only 100 mM. In addition, prior to the instant invention, nucleophilic components have been employed in large excesses (2 to 20-fold) in order to increase the selectivity of the reaction and thereby improve the yield. In chemical syntheses of short-chain peptides in liquid phase, the substrate and nucleophile are normally employed in high and in virtually stoichiometric concentrations. Employing the substrate and nucleophile in such concentrations has not hitherto been possible for the regio- and stereospecific enzymatic peptide syntheses of the present invention.

SUMMARY OF THE INVENTION

Accordingly, it is an object of the present invention to provide a process wherein regio- and stereospecific enzymatic peptide synthesis reactions can be carried out at comparatively high concentrations of the substrate, and wherein the excess of nucleophilic components heretofore required can be drastically reduced.

In accomplishing the foregoing objective, there has been provided, in accordance with one aspect of the present invention, a process for the preparation of protected and unprotected di- or oligopeptides, comprising the steps of (A) reacting, in an aqueous solution and in the presence of a hydrolase, a compound of the Formula I $$X-E-R^1 \qquad (I)$$

as an electrophile, wherein E is an amino acid, di- or oligopeptide or a derivative thereof, and where E is N-terminally substituted with X and C-terminally substituted with $R^1$, $R^1$ is an alkoxy group with 1-4 C atoms or an aryl alkoxy group and X is a group which, at the pH values used for the reaction, increases the solubility in water by a factor of $>5$ compared with compounds with $X=H$, in a concentration of at least 100 mM when X is maleyl, with a compound of the Formula II $$H_2N-Q-R^2 \qquad (II)$$

as a nucleophile, wherein Q is one selected from the group consisting of (i) an amino acid (ii) a di- or oligopeptide and (iii) an amino-acid, dipeptide or oligopeptide derivative, and where Q is C-terminally substituted with $R^2$, $R^2$ is a hydroxy group, an alkoxy group with 1-4 C atoms, an aryl alkoxy group or an $NR^3R^4$, $R^3$ and $R^4$ are each, independently of one another, hydrogen, a $C_1$-$C_4$-alkyl radical, an aryl radical or an aryl alkyl radical optionally; and (B) removing protective groups from the reaction product or from the reaction product which has separated out of the reaction mixture.

In accordance with another aspect of the present invention, a process for the preparation of protected or unprotected di- or oligopeptides as described in the preceding paragraph has been provided wherein X in the Formula I is a group of the Formula III

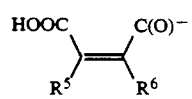

wherein $R^5$ and $R^6$ are each, independently of one another, H, a $C_1$-$C_4$-aryl, heteroaryl, arylalkyl or heteroaryl-alkyl radical or, with inclusion of the double bond, together form an optionally substituted aromatic or alicyclic ring which can also be saturated where appropriate.

In accordance with yet another aspect of the present invention, a process is provided for the production of protected or unprotected di- or oligopeptides, the process comprising reacting enzymatically a compound of the Formula I $$X-E-R^1 \qquad (I)$$

as an electrophile, wherein E is an amino acid, di- or oligopeptide or a derivative thereof, and where is E is substituted N-terminally with X and C-terminally with $R^1$, with a compound of the Formula II $$H_2N-Q-R^2 \qquad (II)$$

as a nucleophile, wherein Q is an amino acid, di- or oligopeptide or a derivative thereof, and where Q is substituted C-terminally with $R^2$, in aqueous solution in the presence of a hydrolase (E.C. 3.4 . . . ) wherein the electrophile is present in a concentration greater than or equal to 50 mM, or, in the case of X=maleyl, greater than or equal to 100 mM, and wherein, at the pH-value used for said reaction, at least one of the groups X, $R^1$, and $R^2$ or the two groups X and $R^1$ together increases the solubility in water by a factor of greater than 5, wherein A) X increases the solubility in water in comparison to the compound in Formula V $$E-R^1 \qquad (V)$$

wherein E is an amino acid, di- or oligopeptide or a derivative thereof, and where E is substituted C-terminally with $R^1$, $R^1$ is not OH, or $R^1$ increases the solubility in water in comparison to the compound in Formula VI

X—E—OCH$_3$ (VI)

wherein E is an amino acid, di- or oligopeptide or a derivative thereof, and where E is substituted N-terminally with X and C-terminally with OCH$_3$, $R^1$ is not OH, or X and $R^1$ together increase the solubility in water in comparison to the compound in Formula VII

H$_3$C—C(O)—E—OCH$_3$ (VII)

wherein E is an amino acid, di- or oligopeptide or a derivative thereof, and where E is substituted N-terminally with H$_3$C—C(O) and C-terminally with OCH$_3$, X is not H and $R^1$ is not OH, and/or wherein B) $R^2$ increases the solubility in water in comparison to the compound in Formula VIII

Q—OCH$_3$ (VIII)

wherein Q is an amino acid, di- or oligopeptide or a derivative thereof, and where Q is substituted C-terminally with OCH$_3$ and $R^2$ is not OH.

In accordance with yet a further aspect of the present invention, a process is provided for the preparation of protected or unprotected di- or oligopeptides, comprising the steps of (A) reacting, in an aqueous solution in the presence of a hydrolase, an N-betainyl-amino acid alkyl ester or di- or oligopeptide alkyl ester of the Formula IV

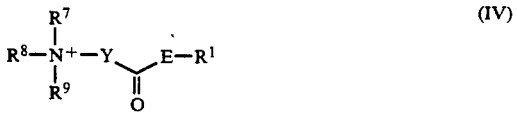

(IV)

wherein

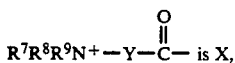
$R^7R^8R^9N^+$—Y—C— is X, and X is a group which, at the pH values used for the reaction, increases the solubility in water by a factor >5 compared with X=H, E is an amino acid, di- or oligopeptide or a derivative thereof, and where E is N-terminally substituted with X and C-terminally substituted with $R^1$, $R^1$ is an alkoxy group with 1–4 C atoms or an arylalkoxy group, Y is an alkylene group with 1–4 C atoms, arylene or aralkylene group, and $R^7$, $R^8$ and $R^9$ are each, independently of one another, an alkyl radical with 1–4 C atoms or an aryl radical which can both be optionally substituted with a compound of the Formula II

H$_2$N—Q—$R^2$ (II)

as a nucleophile, wherein Q is one selected from the group consisting of (i) an amino acid (ii) a di- or oligopeptide and (iii) an amino-acid, dipeptide or oligopeptide derivative and where Q is C-terminally substituted with $R^2$, $R^2$ is a hydroxy group, an alkoxy group with 1–4 C atoms, an aryl alkoxy group or an $NR^3R^4$, $R^3$ and $R^4$ are each, independently of one another, hydrogen, a $C_1$–$C_4$-alkyl radical, an aryl radical or an aryl alkyl radical optionally; and (B) removing protective groups from the reaction product or from the reaction product which has separated out of said reaction mixture.

Other objects, features and advantages of the present invention will become apparent to those skilled in the art from the following detailed description. It is to be understood, however, that the detailed description and specific examples, while indicating preferred embodiments of the present invention, are given by way of illustration and not limitation. Many changes and modifications within the scope of the present invention may be made without departing from the spirit thereof, and the invention includes all such modifications.

BRIEF DESCRIPTION OF THE DRAWINGS

FIG. 1 shows that yields of Tyr-Arg synthesized by a process within the present invention are approximately 10 times the yield obtained by prior art processes.

FIG. 2 shows the results of continuous enzymatic synthesis of Mal-Tyr-Arg-OEt as a function of residence times.

DETAILED DESCRIPTION OF THE PREFERRED EMBODIMENTS

It has been discovered that the solubility and reactivity in water of amino acid alkyl esters and peptide alkyl esters can be increased by N-terminal protective groups which are extremely polar and, preferably, carry a charge. It has been further discovered that solubility can be increased to such a great extent (5- to 100-fold for tyrosine ethyl ester, for example) that substrate concentrations greater than 50 mM, preferably greater than 100 mM, in most cases up to 1M, but also up to, for instance, 4M, can be used in preferably homogeneous aqueous phase, and that these high substrate concentrations surprisingly result in an unexpectedly superior increase in enzyme activity.

It is thus possible using a process within the invention to achieve extremely high space-time yields. For example, when employing a process within the present invention, yields for the synthesis of protected Tyr-Arg (FIG. 1) are increased by a factor of 10 when compared to prior art processes. Another unexpectedly superior result achieved by employing the drastically increased substrate concentrations according to a process within the present invention is that the concentration of nucleophilic component can be reduced to equimolar amounts with a negligible reduction in the selectivity of the aminolysis reaction versus the hydrolysis reaction. Preferably, the molar ratio of the compound of Formula II to the compound of Formula I does not exceed 1.5. In a further preferred embodiment, the molar ratio falls between 0.8 to 1.2 and is more preferably about 1.0. Reactants derived from natural α-amino acids are particularly useful in a process within the present invention. Polar groups are suitable as N-terminal and/or C-terminal protective groups, preferably those carrying a charge. Polar groups are defined as functionalized groups with an electron density distribution causing a high affinity to water and increasing the hydrophilic character of the electrophile.

A positive or negative charge on the protective group plays no part in its choice. Thus, it is possible to employ at the N-terminus, carboxyl-substituted acyl groups, such as phthalyl or maleyl, and derivatives and homologs thereof. Such groups are easily introduced chemically and, subsequent to the peptide synthesis, removed under mild conditions with, for example, acid catalysis.

Although investigations of the substrate specificity of α-chymotrypsin (α-CT) were carried out some time ago and included the use of N-maleylamino acid esters for dipeptide synthesis, the only substrate concentrations used were the customary low concentrations in water, typically 0.01 to a maximum of 93 mM. (V. Schellenberger, U. Schellenberger, H.-D. Jakubke, Coll. Czech. Chem. Commun. 53:2884 (1988)). The enormously beneficial effect of increasing the substrate concentration made possible by the introduction of a highly polar protective group according to the present invention was not recognized.

Exemplary of electrophilic reactants having a positively charged protective group which are suitable for use within the present invention are the hitherto unknown N-betainyl-amino acid esters and -peptide esters of the Formula IV

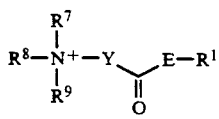
(IV)

wherein

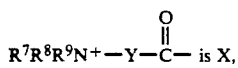

and X is a group which, at the pH values used for the reaction, increases the solubility in water by a factor >5 compared with X=H, E is an amino acid, di-or oligopeptide or a derivative thereof, and where E is N-terminally substituted with X and C-terminally substituted with $R^1$, $R^1$ is an alkoxy group with 1–4 C atoms or an arylalkoxy group, Y is an alkylene group with 1–4 C atoms, arylene or aralkylene group, and $R^7$, $R^8$ and $R^9$ are each, independently of one another, an alkyl radical with 1–4 C atoms or an aryl radical which can both be optionally substituted. These derivatives can be easily prepared by aminolysis of the corresponding halogenoacyl compounds with trialkylamines. The betainyl compounds wherein Y is a —$CH_2$— can be obtained, for example, by reacting known N-chloroacetylamino alkyl esters with trialkylamines.

Exemplary of enzymes suitable for use within the present invention are all hydrolases suitable for peptide syntheses (E.C. 3.4 ... ), such as α-chymotrypsin, subtilisin; carboxypeptidase W, C and Y; trypsin; papain, ficin and bromelain. In a preferred embodiment, α-chymotrypsin is utilized when a derivative of an aromatic amino acid, for example, tyrosine, phenylalanine or tryptophan, is employed as the electrophilic reactant. In a particularly preferred embodiment favoring the further treatment of the resulting reaction mixture, papain is employed under standard conditions when reacting a Formula I component with a component of Formula II wherein $R^2$ is a free acid group. While the substrate concentration can be increased above 1M up to concentrations of 4–5M, in a preferred embodiment concentrations in the range of from 0.5 to 1M are preferred.

In another preferred embodiment, electrophile/hydrolase ratios of $10^5$ to $10^7$ (M/M) are employed. The reaction times using such ratios are not substantially longer than in conventional processes wherein such ratios are usually $10^2$ to $10^4$. If papain is used as the hydrolase, a ratio of greater than $10^3$ is employed.

A process within the present invention can be carried out continuously or in batches. When carried out continuously, for example in an enzyme membrane reactor (EMR), conversions of greater than 95% can be achieved with residence times of less than 20 minutes, especially if the above mentioned ratio is used.

Surprisingly, it has also been found that when E in Formula I is tyrosine, phenylalanine or tryptophan, and when X in Formula I is an optionally lower alkylated (i.e., $C_1$–$C_4$ alkylated) maleyl radical or an optionally substituted phthalyl radical, and an arginine alkyl ester is employed as the nucleophile, the protected dipeptide derivative usually precipitates out of the aqueous reaction solution and can, therefore, be easily separated from the remaining reactants in solution. Similar advantages can be obtained if mainly $R^1$ in the electrophile serves as a solubility-increasing group. $R^1$ is cleaved off during the reaction, resulting in a diminished solubility of the desired product, possibly causing precipitation thereof.

In cases where the solubility of the nucleophile in water is too limited, it is possible in another preferred embodiment of the present invention to increase the solubility by introducing a group, for example a choline ester group, which carries a charge at the pH values used for the reaction.

Without further elaboration, it is believed that one skilled in the art can, using the preceding description, utilize the present invention to its fullest extent. The following examples are to be construed as merely illustrative, therefore, and not limitative of the remainder of the disclosure in any way whatsoever.

EXAMPLE 1

Synthesis of N-maleylamino Acid Ethyl Ester

Preparation of N-maleylamino acid ethyl esters was carried out by the method of Atassi et al. (Methods of Enzymology 25:546 (1972)). Ethyl esters of tyrosine, phenylalanine, tryptophan, alanine and arginine were reacted.

In each case 200 mmol of the amino acid ester hydrochlorides was dissolved in 500 ml of $H_2O$ and the resulting solution was adjusted to pH 8.2 with NaOH. At room temperature, 300 mmol of maleic anhydride was added in portions, while the pH was maintained at pH 8.2 with 5N NaOH. After the addition was complete, the reaction solution was stirred at room temperature at pH 8.2 for an additional 30 minutes. The conversion was checked by HPLC and showed quantitative conversion in every case.

A solution obtained by this process can be employed directly for the enzymatic synthesis. A solid product contaminated with sodium chloride and maleic acid can be obtained by freeze drying.

Investigations of the solubility in water (autogenous pH) produced the following results:

| | |
|---|---|
| Mal-Tyr-OEt: > 600 mM | Mal-Ala-OEt: > 1900 mM |
| Mal-Phe-OEt: > 700 mM | Mal-Arg-OEt: > 1000 mM |
| Mal-Trp-OEt: > 700 mM | |

EXAMPLE 2

Synthesis of N-citraconylamino Acid Ethyl Ester

Preparation of N-citraconylamino acid ethyl esters was carried out according to the methodology of Example 1 except that citraconic anhydride was employed in place of maleic anhydride.

Investigations of the solubility in water (autogenous pH) produced the following results:

Cit-Tyr-OEt: >1000 mM

Cit-Phe-OEt: >1000 mM

Cit-Trp-OEt: >900 mM

EXAMPLE 3

Synthesis of N-phthalylamino Acid Ester

The preparation was carried out in analogy to Example 1 except that phthalic anhydride was employed in place of maleic anhydride. The ethyl esters of tyrosine, alanine and arginine were reacted.

Investigations of the solubility in water (autogenous pH) produced the following results:

Phthal-Tyr-OEt: >800 mM

Phthal-Ala-OEt: >1800 mM

Phthal-Arg-OEt: >800 mM

EXAMPLE 4

Synthesis of N-trimellitylamino Acid Ester (TMA Ester)

Preparation of N-trimellitylamino acid ester was carried out according to the methodology of Example 1 except that trimellitic anhydride was employed in place of maleic anhydride. The ethyl ester of tyrosine was reacted. Solubility in water was found to be greater than 1000 mM.

EXAMPLE 5

Synthesis of N-(trimethylammoniumacetyl)amino Acid Ethyl Ester Hydrochloride

The appropriate chloroacetyl compounds (ClAc-Tyr-OEt 60 mmol; ClAc-Phe-OEt 100 mmol; ClAc-Trp-OEt 100 mmol) were dissolved in 250 ml of THF in a 500 ml 3-necked flask with mechanical stirrer, condenser, thermometer and gas-introduction tube, and gaseous trimethylamine passed in. The reaction solution was refluxed for 6 h in each case, during which the relevant betaine amino acid ethyl ester hydrochlorides precipitated. After the reaction was complete, the product was filtered off, thoroughly washed with THF and dried over $P_2O_5$. N-(trimethylammoniumacetyl)-L-tyrosine ethyl ester chloride ($C_{16}H_{25}ClN_2O_4$):
  Yield: 35% of theoretical yield
  Calculated: C 55.73 H 7.31 N 8.12 Cl 10.29
  Found: C 55.56 H 7.31 N 8.41 Cl 10.42

$^1$H-NMR (CDCl$_3$): 1.15 (t, 3H), 2.70–3.00 (m, 2H), 3.17 (s, 9H), 4.08 (q, 2H), 4.17 (d, 1H), 4.27 (d, 1H), 4.45 (m, 1H), 6.66 (d, 2H), 7.03 (d, 2H), 9.35 (br, s, 2H).

N-(trimethylammoniumacetyl)-L-phenylalanine ethyl ester chloride ($C_{16}H_{25}ClN_2O_3$):
  Yield: 58% of theoretical yield
  Calculated: C 58.44 H 7.66 N 8.51 Cl 10.79
  Found: C 58.39 H 7.89 N 8.61 Cl 10.89

$^1$H-NMR (CDCl$_3$): 1.27 (t, 3H), 3.00–3.35 (m, 2H), 3.32 (s, 9H), 4.18 (q, 2H), 4.51 (d, 1H), 4.69 (m, 1H), 4.94 (d, 1H), 7.12–7.30 (m, 3H), 7.42 (m, 2H), 9.90 (d, 1H).

N-(trimethylammoniumacetyl)-L-tryptophan ethyl ester chloride ($C_{16}H_{26}ClN_3O_3$):
  Yield: 100% of theoretical yield
  Calculated: C 58.77 H 7.12 N 11.42 Cl 9.65
  Found: C 57.96 H 7.56 N 10.69 Cl 9.42

$^1$H-NMR (CDCl$_3$): 1.26 (t, 3H), 3.05 (s, 9H), 3.20–3.45 (m, 2H), 4.18 (q, 2H), 4.38 (d, 1H), 4.58 (d, 1H), 4.72 (m, 1H), 7.08 (m, 2H), 7.38 (m, 1H), 7.54 (m, 2H), 9.37 (d, 1H), 9.91 (s, 1H).

Investigations regarding solubility showed that all three betaine amino acid ethyl ester hydrochlorides were soluble in water in concentrations greater than 4M.

EXAMPLE 6

Synthesis of N-(trimethylammoniumpropionyl, BetProp)amino Acid Ethyl Ester Hydrochlorides Preparation of N-(trimethylammoniumpropyl, BetProp) amino acid ethyl ester hydrochlorides was carried out according to the methodology of Example 5 except that chloropropyl compound was employed in place of the corresponding chloroacetyl compound. The ethyl ester of tyrosine was reacted. Solubility in water was found to be greater than 1000 mM.

EXAMPLE 7

Synthesis of N-(trimethylammoniumbutyryl, BetBut)amino Acid Ethyl Ester Hydrochlorides Preparation of N-(trimethylammoniumbutyl, BetBut)amino acid ethyl ester hydrochlorides was carried out according to the methodology of Example 5 except that a chlorobutyl compound was employed in place of the corresponding chloroacetyl compound. The ethyl ester of tyrosine was reacted. Solubility in water was found to be greater than 2200 mM.

EXAMPLE 8

Determination of the Activities and Selectivities of the Enzymatic Reactions of N-maleyl-, N-citraconyl-, N-phthalyl-, N-trimellityl-, N-(trimethylammoniumacetyl)-, N-(trimethylammoniumpropyl)- and N-(trimethylammoniumbutyryl)-amino Acid Ethyl Esters With Arginine, Arginine Ethyl Ester and Argininamide Enzymatic dipeptide synthesis The enzymes employed were α-chymotrypsin (α-CT), carboxypeptidase Y (CPD-Y) and papain whose pH and temperature optima for dipeptide synthesis are known, pH 9.5; T=25° C. for CT; pH 9.0; T=25° C. for CPD-Y and papain. The dipeptide syntheses were all carried out under the foregoing reaction conditions using equimolar concentrations of substrate and nucleophile in each case.

In each case, the substrate and nucleophile concentrations were 500 or 300 mM when Arg-NH$_2$ was used, and 600 or 300 mM when Arg-OEt was used. In addition, the reaction with 300 mM free arginine was carried out using papain. The electrophile/hydrolase ratios (M/M) were $1.1\times10^7$ (CT) and $3\times10^5$ (CPD-Y) with Arg-NH$_2$ as the nucleophile, $2.4\times10^7$ (CT) with Arg-OEt and $5.3\times10^3$ (papain) with Arg-OH as the nucleophile.

The initial activities and selectivities determined by standard methods using these reaction parameters are listed in the following table.

TABLE 1

|   | Dipeptide | Enzyme | Selectivity | Initial activity |
|---|---|---|---|---|
| 1 | Mal-Tyr-Arg-NH$_2$ | α-CT | 47% | 1500 U/mg |
| 2 | Mal-Phe-Arg-NH$_2$ | α-CT | 18% | 155 U/mg |
| 3 | Cit-Trp-Arg-NH$_2$ | α-CT | 22% | 410 U/mg |
| 4 | Mal-Trp-Arg-NH$_2$ | α-CT | 42% | 1420 U/mg |
| 5 | Bet-Tyr-Arg-NH$_2$ | α-CT | 29% | 800 U/mg |
| 6 | Bet-Phe-Arg-NH$_2$ | α-CT | 42% | 2200 U/mg |
| 7 | Cit-Phe-Arg-NH$_2$ | α-CT | 41% | 1100 U/mg |
| 8 | Bet-Trp-Arg-NH$_2$ | α-CT | 13% | 195 U/mg |
| 9 | Mal-Tyr-Arg-OEt | α-CT | 80% | 3750 U/mg |
| 10 | Cit-Tyr-Arg-NH$_2$ | α-CT | 78% | 2700 U/mg |
| 11 | Bet-Tyr-Arg-NH$_2$ | CPD-Y | 44% | 57 U/mg |
| 12 | Bet-Phe-Arg-NH$_2$ | CPD-Y | 52% | 185 U/mg |
| 13 | Bet-Trp-Arg-NH$_2$ | CPD-Y | 29% | 29 U/mg |
| 14 | Phthal-Tyr-Arg-NH$_2$ | α-CT | 90% | 900 U/mg |
| 15 | Phthal-Tyr-Arg-OEt | α-CT | 70% | 190 U/mg |
| 16 | TMA-Tyr-Arg-NH$_2$ | α-CT | 85% | 18 U/mg |
| 17 | TMA-Tyr-Arg-OEt | α-CT | 70% | 12 U/mg |
| 18 | BetProp-Tyr-Arg-NH$_2$ | α-CT | 50% | 2200 U/mg |
| 19 | BetBut-Tyr-Arg-NH$_2$ | α-CT | 70% | 2500 U/mg |
| 20 | Phthal-Ala-Arg | Papain | 63% | |

With respect to reactions 14 to 19, in each case the reactions were carried out in concentrations of 300 mM. The electrophile/hydrolase rations (M/M) employed were $6.3\times10^6$ (CT) with Arg-NH$_2$ and $8.3\times10^6$ (CT) with Arg-OEt.

EXAMPLE 9

Enzymatic Synthesis of Mal-Tyr-Lys-OEt

Mal-Tyr-Lys-OEt was prepared with CT as the catalyst in a 100 ml beaker with Mal-Tyr-OEt employed as the electrophile and Lys-OEt.2 HCl employed as the nucleophile. After a short time, the product separated out as a white precipitate and was filtered off, washed with water and dried in a vacuum at 50° C. The conditions and results employed are compiled in the following table:

TABLE 2

| Electrophile/nucleophile ratio: | 1:1 |
|---|---|
| Substrate concentration: | 0.4M each |
| Substrate/enzyme ratio: | $1.5 \times 10^6$ |
| pH: | 9.5 |
| Temperature: | 25° C. |
| Reaction time: | 10 minutes |
| Isolated yield: | 81% |
| Space-time yield: | 19.5 kg/(l.d) |
| Spec. enzyme activity: | 4042 U/mg |

EXAMPLE 10

Preparation of Mal-Tyr-Ala-Gln

It is also possible according to the present invention to employ an unprotected dipeptide as nucleophile. A protected tripeptide, Mal-Tyr-Ala-Gln, was prepared using CT as the catalyst, Mal-Tyr-OEt as the electrophile and a dipeptide, Ala-Gln, as the nucleophile. The reaction time was 20 minutes, and no further decrease in Ala-Gln was recorded in the HPLC after 6 minutes. The product was separated from Ala-Gln on an M 600 (Lewatit) anion exchanger and identified by $^1$H-NMR (solvent: D$_2$O). The yield was 71.5%.

| Electrophile/nucleophile ratio: | 1:1 |
|---|---|
| Substrate concentration: | 0.43M each |
| Substrate/enzyme ratio: | $2.9 \times 10^5$ |
| pH: | 9.5 |
| Temperature: | 25° C. |

EXAMPLE 11

Preparation of Mal-Tyr-Orn-OEt

It is also possible according to the present invention to employ a non-proteinogenic amino acid as a nucleophile. Mal-Tyr-OEt, an electrophile, and Orn-OEt.2HCl, a nucleophile, were reacted using α-CT as a catalyst. After a reaction time of 20 minutes, the solution was concentrated, the enzyme was separated off by ultrafiltration with a membrane with MWCO 10,000, and the dissolved fraction was lyophilized. Both Mal-Tyr-Orn and the Orn delta-lactam cyclization product were isolated by preparative HPLC and identified by $^1$H-NMR. The combined yield of the two products (about 1:1) was about 45–50%.

| Electrophile/nucleophile ratio: | 1:1 |
|---|---|
| Substrate concentration: | 0.26M each |
| Substrate/enzyme ratio: | $6.5 \times 10^5$ |
| pH: | 9.5 |
| Temperature: | 25° C. |

EXAMPLE 12

Preparation of H-Tyr-Cit-OEt

It is also possible according to the present invention to employ a non-basic amino acid as a nucleophile. Tyr-Cit-OEt was prepared in a 100 ml beaker using α-CT as the enzyme, Mal-Tyr-OEt as the electrophile and citrulline ethyl ester (Cit-OEt) as the nucleophile. After a reaction time of 30 minutes, the enzyme was separated off in an ultrafilter (10,000 MWCO), and the product was detected along with the precursors Mal-Tyr-OEt and Cit-OEt, as well as H-Tyr-OEt in equal parts by Liquid Chromatography-Mass Spectroscopy (LC-MS).

| Electrophile/nucleophile ratio: | 1:1 |
|---|---|
| Substrate concentration: | 0.12M each |
| Substrate/enzyme ratio: | $1.5 \times 10^6$ |
| pH: | 10.2 |
| Temperature: | 25° C. |

EXAMPLE 13

Preparation of Mal-Tyr-Lys-Ala-OMe

In addition to the serine proteases, it is also possible according to the present invention to use a thiol protease (papain) as the enzyme, as well as a protected dipeptide (Mal-Tyr-Lys-OEt) as the electrophile. The product was prepared using Mal-Tyr-Lys-OEt as the electrophile and Ala-OMe as the nucleophile and papain as the catalyst in aqueous suspension. After a reaction time of 75 minutes, 49% of Mal-Tyr-Lys-OEt was still present. The suspension filtrate was ultrafiltered through a 10,000 MWCO membrane module, and the product was detected by LC-MS.

| Electrophile/nucleophile ratio: | 1:1 |
|---|---|
| Substrate concentration: | 0.13M each |
| Substrate/enzyme ratio: | $1.9 \times 10^3$ |
| pH: | 9.6 |
| Temperature: | 25° C. |

EXAMPLE 14

Continuous Enzymatic Synthesis of Mal-Tyr-Arg-OEt

Mal-Tyr-Arg-OEt was prepared continuously for 7 hours in a 10 ml enzyme membrane reactor. The operating conditions employed are compiled below:

| Enzyme: | α-chymotrypsin |
|---|---|
| Enzyme concentration: | 0.2 mg/ml |
| Mal-Tyr-OEt: | 600 mM |
| Arg-OEt: | 600 mM |
| pH: | 9.5 |
| Temperature: | 25° C. |
| Residence time: | 12 min |
| Flow rate: | 50 ml/h |
| Reactor volume: | 10 ml |
| Mean conversion: | about 98% |
| Mean selectivity: | about 80% |
| Space-time yield: | 13.36 kg/(l.d) |
| Enzyme consumption: | 97 mg/kg of product |

The conversions and selectivities achievable in this test as a function of the set residence times are depicted in FIG. 2.

The protected dipeptide precipitated out of the discharged product solution in the precooled collecting vessel and, after filtration and washing several times with water, was shown to have a purity greater than 97%.

$^1$-NMR (D$_2$O+DCl): 1.08 (t, 3H), 1.42 (m, 2H), 1.57 (m, 1H), 1.72 (m, 2H), 2.89 (m, 2H), 3.02 (m, 2H), 4.01 (q, 2H), 4.21 (m, 1H), 4.46 (m, 1H), 6.18 (d, 1H), 6.34 (d, 1H), 6.69 (d, 1H), 7.01 (d, 1H).

EXAMPLE 15

Batch Enzymatic Synthesis of Mal-Tyr-Arg-OEt

In a batch procedure (300 l), Mal-Tyr-OEt (0.25M) and Arg-OEt (0.25M) are reacted with α-chymotrypsin (0.025 mg/ml) at pH 9.5 and 25° C. After 2 hours, filtration of the precipitate and washing with water result in 26.0 kg of Mal-Tyr-Arg-OEt (75% of theoretical yield) with an HPLC purity greater than 97%.

A process within the present invention has proven to be provide unexpectedly superior results for the economic preparation of di- and oligopeptides by reacting N-terminally protected amino acid esters with amino acid esters or di- or oligopeptide esters or amides or the corresponding free acids.

EXAMPLE 16

Synthesis of Benzyloxycarbonylamino Acid Choline Ester Iodide

The synthesis was carried out according to a published procedure (Coll. Czech. Chem. Comm. 53:2884(1988)). Different benzyloxycarbonyl amino acids were esterified with equimolar amounts of 2-dimethlaminoethanol in ethyl acetate with addition of dicyclohexylcarbodiimide. After 30 minutes, dicyclohexylurea was filtered off and the ester product precipitated with ether. Subsequently, this product was dissolved in methyl iodide without further characterization. After 2 days, the excess of methyl iodide was evaporated under vacuum. The resulting amino acid choline ester iodides were then recrystallized from ethanol.

Alternatively, a sulfonic acid group can be introduced as an anionic residue. An expert skilled in the art can access other charged or polar groups without difficulty according to above-mentioned procedure.

EXAMPLE 17

Enzymatic Dipeptide Synthesis With Benzyloxycarbonylphenylalanine Choline Ester

Benzyloxycarbonyl-phenylalanine choline ester was reacted with an equimolar amount of arginine amide as nucleophile using α-CT as the hydrolase. The product, benzyloxycarbonyl-phenylalanine-arginine amide was identified by HPLC.

EXAMPLE 18

Dipeptides With C-terminal Anionically-charged Soluble Protective Group (Ethanesulfonic Acid Ester): Formation of Mal-Tyr-Ala-O(CH$_2$)$_2$-OSO$_3^-$ Mal-Tyr-OEt as the electrophile was reacted with alanine ethylsulfonic acid ester (Ala-O(CH$_2$)2-OSO$_3^-$) as the nucleophile and α-CT as the hydrolase in a 100 ml beaker to yield Mal-Tyr-Ala-O(CH$_2$)$_2$-OSO$_3^-$. After a reaction time of 40 minutes had elapsed, no further change was observed by HPLC. The enzyme was separated with an ultrafiltration module (10.000 MWCO) and the product was identified together with equal amounts of the reactants Mal-Tyr-OEt and Ala-O(CH$_2$)$_2$-OSO$_3$ via LC-MS.

| Electrophile-nucleophile ratio: | 1:1 |
|---|---|
| Substrate concentration: | 0.29M each |
| Substrate-enzyme ratio: | $5.6 \cdot 10^5$ |
| pH-value: | 9.5 |
| Temperature: | 25° C. |

EXAMPLE 19

Dipeptides With C-terminal Anionically-charged Soluble Protective Group (Ethanesulfonic Acid Ester) on the Electrophile: Formation of N-Ac-Tyr-Arg-OEt N-Ac-Tyr-O(CH$_2$)$_2$-OSO$_3^-$ as an electrophile and arginine ethyl ester (Arg-OEt) as a nucleophile were reacted in a 100 ml beaker with α-CT as the hydrolase to yield N-Ac-Tyr-Arg-OEt. After several minutes, the product precipitated as white crystals and was filtered off, washed with cold water, and dried in a vacuum oven at 50°.

| Electrophile-nucleophile ratio: | 1:1 |
|---|---|
| Substrate concentration: | 0.38M each |
| Substrate-enzyme ratio: | $9.6 \cdot 10^5$ |
| pH-value: | 9.5 |
| Temperature: | 25° C. |
| Reaction time: | 20 minutes |
| Isolated yield: | 63% |

What is claimed is:

1. A process for the preparation of protected dipeptides or oligopeptides, comprising the steps of (A) reacting, in an aqueous solution in the presence of a protease of the group E.C. 3.4 and in a concentration greater than 100 mM, a compound of the Formula I $$X—E—R^1 \qquad (I)$$

as an electrophile, wherein E is an amino acid, dipeptide or oligopeptide, and where E is N-terminally substituted with X and C-terminally substituted with $R^1$, $R^1$ is an alkoxy group with 1–4 C atoms or an aryl alkoxy group and X is a protective group with carries a charge in the aqueous solution,
with a compound of the Formula II $$H_2N—Q—R^2 \qquad (II)$$

as a nucleophile, wherein Q is selected from the group consisting of (i) a residue of an amino acid (ii) a residue of a dipeptide or oligopeptide and (iii) a residue of an amino-acid, dipeptide or oligopeptide derivative, where $R^2$ is selected from the group consisting of a hydroxy group, an alkoxy group with 1–4 C atoms, an aryl alkoxy group and $NR^3R^4$, where $R^3$ and $R^4$ are each, independently of one another, hydrogen, a $C_1$-$C_4$-alkyl radical, an aryl radical or an aryl alkyl radical and wherein the molar ratio of said nucleophile of said Formula II to said electrophile of Formula I is less than 1.5.

2. The process as claimed in claim 1, wherein said compound of said Formula I is employed in a concentration ranging from 100 mM to 1000 mM.

3. A process according to claim 1, wherein the molar ratio of said compound of Formula I to protease is $>10^5$.

4. A process according to claim 1, wherein said protease is papain and the molar ratio of said compound of Formula I to said papain is $>10^3$.

5. A process according to claim 1, wherein said reaction is carried out continuously with a residence time of less than 20 minutes.

6. A process according to claim 1, wherein $R^2$ in Formula II is a group carrying a charge.

7. A process according to claim 1, wherein α-chymotrypsin is the protease when E in said Formula I is an aromatic amino acid.

8. A process according to claim 1, wherein α-chymotrypsin is the protease when E in said Formula I is an aromatic amino acid selected from the group consisting of L-tyrosine, L-phenylalanine and L-tryptophan.

9. A process according to claim 1, wherein X in Formula I is a group of the Formula III

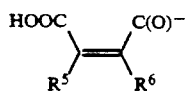

$$(III)$$

wherein $R^5$ and $R^6$ are each, independently of one another, H, a $C_1$-$C_4$-alkyl, aryl, heteroaryl, arylalkyl or heteroaryl-alkyl radical or, with inclusion of the double bond, together form an optionally substituted aromatic or alicyclic ring which can also be saturated where appropriate.

10. A process for the preparation of protected dipeptides or oligopeptides, comprising the steps of
(A) reacting, in an aqueous solution in the presence of a protease of the group E.C. 3.4, an N-betainyl-amino acid ester or dipeptide or oligopeptide ester of the Formula IV

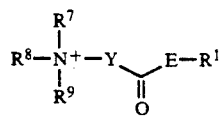

$$(IV)$$

wherein, E is a residue of an amino acid, dipeptide or oligopeptide, that is C-terminally substituted with $R^1$, $R^1$ being an alkoxy group with 1–4 C atoms or an arylalkoxy group, Y being an alkylene group with 1–4 C atoms, arylene or aralkylene group, and $R^7$, $R^8$ and $R^9$ being each, independently of one another, an alkyl radical with 1–4 C atoms or an aryl radical, either of which can be optionally substituted,
with a compound of the Formula II $$H_2N—Q—R^2 \qquad (II)$$

as a nucleophile, wherein Q is one selected from the group consisting of (i) a residue of an amino acid (ii) a residue of a dipeptide or oligopeptide and (iii) a residue of an amino-acid, dipeptide or oligopeptide derivative, and wherein $R^2$ is a hydroxy group, an alkoxy group with 1–4 C atoms, an aryl alkoxy group or $NR^3R^4$, $R^3$ and $R^4$ being each, independently of one another, hydrogen, a $C_1$-$C_4$-alkyl radical, an aryl radical or an aryl alkyl radical.

11. A process according to claim 3, wherein said reaction is carried out continuously with a residence time of less than 20 minutes.

12. A process according to claim 4, wherein said reaction is carried out continuously with a residence time of less than 20 minutes.

13. A process for the preparation of protected dipeptides or oligopeptides, comprising enzymatic reaction of a compound of the Formula I $$X—E—R^1 \qquad (I)$$

as an electrophile, wherein E is a residue of an amino acid, dipeptide or oligopeptide, and where E is substituted N-terminally with a protective group, X, which carries a charge in the aqueous solution and C-terminally with $R^1$, where $R^1$ is an alkoxy group with 1–4 C atoms or an aryl alkoxy group, with a compound of the Formula II $$H_2N—Q—R^2 \qquad (II)$$

an a nucleophile, wherein Q is a residue of an amino acid or a residue of a dipeptide or oligopeptide, and where $R^2$ is a hydroxy group, an alkoxy group with 1–4 C atoms, an aryl alkoxy group or a group $NR^3R^4$ in which $R^3$ and $R^4$ are each, independently of one another, hydrogen, a $C_1$-$C_4$-alkyl radical, an aryl radical or an aryl alkyl radical, in aqueous solution in the presence of a protease of group E.C. 3.4, wherein the electrophile is present in a concentration greater than or equal to 300 mM, and wherein the molar ratio of said nucleophile of said Formula II to said electrophile of said Formula I is less than 1.5.

14. The process as claimed in claim 1, wherein protected dipeptide or oligopeptide is recovered from the reaction mixture.

15. The process as claimed in claim 1, wherein the hydrolase is selected from the group consisting of α-chymotrypsin, subtilisin, carboxypeptidase W, carboxypeptidase C, carboxypeptidase Y, trypsin, papain, ficin and bromelain.

16. The process as claimed in claim 1, wherein X is an acyl group that is substituted with a carboxyl group.

17. The process as claimed in claim 16, wherein X is phthalyl, maleyl or citraconyl.

18. A process for the preparation of unprotected dipeptides or oligopeptides, comprising the steps of (A) reacting, in an aqueous solution in the presence of a protease of the group E.C. 3.4 and in a concentration greater than 100 mM, a compound of the Formula I $$X-E-R^1 \quad (I)$$

as an electrophile, wherein E is a residue of an amino acid, a residue of a dipeptide or oligopeptide, and where E is N-terminally substituted with X and C-terminally substituted with $R^1$, $R^1$ is an alkoxy group with 1-4 C atoms or an aryl alkoxy group and X is a charge-bearing protective group, with a compound of the Formula II $$H_2N-Q-R^2 \quad (II)$$

as a nucleophile, wherein Q is selected from the group consisting of (i) a residue of an amino acid (ii) a residue of a dipeptide or oligopeptide and (iii) a residue of an amino-acid, dipeptide or oligopeptide derivative, where Q is C-terminally substituted with $R^2$, $R^2$ being selected from the group consisting of a hydroxy group, an alkoxy group with 1-4 C atoms, an aryl alkoxy group and $NR^3R^4$, where $R^3$ and $R^4$ are each, independently of one another, hydrogen, a $C_1$-$C_4$-alkyl radical, an aryl radical or an aryl alkyl radical and wherein the molar ratio of said nucleophile of said Formula II to said electrophile of Formula I is less than 1.5;

(B) removing protective groups from the reaction product, and (C) recovering unprotected dipeptide or oligopeptide.

19. A process for the preparation of unprotected dipeptide or oligopeptides, comprising the steps of (A) reacting, in an aqueous solution in the presence of a protease of the group E.C. 3.4, an N-betainyl- or betainyl homologous- amino acid ester or dipeptide or oligopeptide alkyl ester of the Formula IV

wherein E is a residue of an amino acid, dipeptide or oligopeptide, and where E is C-terminally substituted with $R^1$, $R^1$ being an alkoxy group with 1-4 C atoms or an arylalkoxy group, Y being an alkylene group with 1-4 C atoms, an arylene or an aralkylene group, and $R^7$, $R^8$ and $R^9$ being each, independently of one another, an alkyl radical with 1-4 C atoms or an aryl radical either of which can be optionally substituted, with a compound of the Formula II $$H_2N-Q-R^2 \quad (II)$$

as a nucleophile, wherein Q is one selected from the group consisting of (i) a residue of an amino acid (ii) a residue of a dipeptide or oligopeptide and (iii) a residue of an amino-acid, dipeptide or oligopeptide derivative, $R^2$ is a hydroxy group, an alkoxy group with 1-4 C atoms, an aryl alkoxy group or an $NR^3R^4$, $R^3$ and $R^4$ are each, independently of one another, hydrogen, a $C_1$-$C_4$-alkyl radical, an aryl radical or an aryl alkyl radical;

(B) removing protective groups from the reaction product, and (C) recovering unprotected dipeptide or oligopepdide.

20. A process for the preparation of unprotected dipeptides or oligopeptides, comprising enzymatic reaction of a compound of the Formula I $$X-E-R^1 \quad (I)$$

as an electrophile, wherein E is a residue of an amino acid, dipeptide or oligopeptide, and where E is substituted N-terminally with X and C-terminally with $R^1$, where $R^1$ is an alkoxy group with 1-4 C atoms or an aryl alkoxy group, with a compound of the Formula II $$H_2N-Q-R^2 \quad (II)$$

as a nucleophile, wherein Q is an amino acid, dipeptide or oligopeptide, and where $R^2$ is a hydroxy group, an alkoxy group with 1-4 C atoms, an aryl alkoxy group or a group $NR^3R^4$ in which $R^3$ and $R^4$ are each, independently of one another, hydrogen, a $C_1$-$C_4$-alkyl radical, an aryl radical or an aryl alkyl radical, in aqueous solution in the presence of a protease of group E.C. 3.4, wherein the electrophile is present in a concentration greater than or equal to 300 mM, and wherein the molar ratio of said nucleophile of said Formula II to said electrophile of said Formula I is less than 1.5;

(B) removing protective groups from the reaction product, and (C) recovering unprotected dipeptide or oligopepdide.

* * * * *